United States Patent
Murthy

(10) Patent No.: US 11,566,217 B2
(45) Date of Patent: Jan. 31, 2023

(54) DUTY CYCLE FOR CELL CULTURE SYSTEMS

(71) Applicant: FLASKWORKS, LLC, Newton, MA (US)

(72) Inventor: Shashi K. Murthy, Newton, MA (US)

(73) Assignee: FLASKWORKS, LLC, Boston, MA (US)

( * ) Notice: Subject to any disclaimer, the term of this patent is extended or adjusted under 35 U.S.C. 154(b) by 78 days.

(21) Appl. No.: 16/539,916

(22) Filed: Aug. 13, 2019

(65) Prior Publication Data

US 2021/0047600 A1 Feb. 18, 2021

(51) Int. Cl.
C12M 3/00 (2006.01)
C12M 1/00 (2006.01)

(52) U.S. Cl.
CPC ............ C12M 29/00 (2013.01); C12M 23/42 (2013.01)

(58) Field of Classification Search
CPC ............... C07K 14/535; C07K 14/545; C07K 14/5412; C07K 14/5406; C07K 14/525; C12N 5/0018; C12N 5/0639; C12M 29/10; C12M 23/42; C12M 25/02; C12M 23/16; C12M 41/14; C12M 1/22; A61K 39/00
See application file for complete search history.

(56) References Cited

U.S. PATENT DOCUMENTS

| | | | |
|---|---|---|---|
| 3,848,569 A | 11/1974 | Folsom | |
| 3,907,687 A | 9/1975 | Hoeltzenbein | |
| 4,939,151 A | 7/1990 | Bacehowski et al. | |
| 5,536,662 A | 7/1996 | Humphries et al. | |
| 5,656,155 A | 8/1997 | Norcross et al. | |
| 6,410,309 B1 | 6/2002 | Barbera-Guillem et al. | |
| 6,607,910 B1 | 8/2003 | Dimitrijevich et al. | |
| 10,647,954 B1 | 5/2020 | Kozbial | |
| 2002/0041868 A1 | 4/2002 | Nicolette et al. | |

(Continued)

FOREIGN PATENT DOCUMENTS

| | | |
|---|---|---|
| AU | 2012/205259 A1 | 8/2012 |
| CA | 2905786 A1 | 10/2014 |

(Continued)

OTHER PUBLICATIONS

Carrier, 2002, Perfusion improved tissue architecture of engineered cardiac muscle, Tissue Eng, 8(2): 175-188.

(Continued)

Primary Examiner — Nathan A Bowers
(74) Attorney, Agent, or Firm — Brown Rudnick LLP; Adam M. Schoen

(57) ABSTRACT

An automated cell culture system with one or more pumps configured to operate on a duty cycle prevents excess heat generation, allowing the cell culture system to operate inside a conventional incubator without overheating. The duty cycle involves switching the pump between on and off modes. By running pumps for a short period of time and then shutting them off, less heat is produced. To account for the reduced pumping time during the cycle, the pump can be run at a higher flow rate while it is on, so that the average flow rate over the course of the cycle is not reduced. Systems of the invention employ duty cycles in which the on-cycle is shorter than the off-cycle, and particularly where the on-cycle is less than 20% of the duration of the entire duty cycle.

11 Claims, 8 Drawing Sheets

(56) References Cited

U.S. PATENT DOCUMENTS

| | | |
|---|---|---|
| 2002/0110905 A1 | 8/2002 | Barbera-Guillem et al. |
| 2003/0036192 A1 | 2/2003 | Singh |
| 2005/0003533 A1 | 1/2005 | Kalinski |
| 2005/0014129 A1* | 1/2005 | Cliffel et al. ...... G01N 33/5038 435/4 |
| 2005/0186669 A1 | 8/2005 | Ho et al. |
| 2006/0019385 A1 | 1/2006 | Smith et al. |
| 2006/0115893 A1 | 6/2006 | Kobayashi et al. |
| 2007/0161051 A1 | 7/2007 | Tsinberg et al. |
| 2008/0032398 A1 | 2/2008 | Cannon et al. |
| 2008/0227176 A1 | 9/2008 | Wilson |
| 2009/0155908 A1 | 6/2009 | Halberstadt et al. |
| 2009/0162853 A1 | 6/2009 | Clark et al. |
| 2012/0077243 A1 | 3/2012 | Niazi |
| 2012/0224450 A1 | 9/2012 | Priestman |
| 2012/0277652 A1 | 11/2012 | Zhao |
| 2013/0095566 A1 | 4/2013 | Oltvai et al. |
| 2013/0309771 A1 | 11/2013 | Gevaert et al. |
| 2014/0065660 A1 | 3/2014 | Kim et al. |
| 2014/0193374 A1 | 7/2014 | Zhao et al. |
| 2014/0295541 A1 | 10/2014 | Nakanishi et al. |
| 2015/0158907 A1 | 6/2015 | Zhou et al. |
| 2015/0204767 A1 | 7/2015 | Taniguchi |
| 2015/0322397 A1* | 11/2015 | Cornforth et al. ...... C12M 25/14 435/293.1 |
| 2016/0145563 A1 | 5/2016 | Berteau et al. |
| 2016/0178490 A1 | 6/2016 | Civel et al. |
| 2016/0215246 A1* | 7/2016 | Goh et al. ............. C12M 23/58 |
| 2016/0272934 A1 | 9/2016 | Chander et al. |
| 2017/0042770 A1 | 2/2017 | Warner et al. |
| 2017/0051238 A1 | 2/2017 | Tanaka et al. |
| 2018/0171296 A1 | 6/2018 | Murthy et al. |
| 2018/0251723 A1 | 9/2018 | Murthy |
| 2020/0157484 A1 | 5/2020 | Kozbial |
| 2020/0231918 A1 | 7/2020 | Kozbial |
| 2020/0308523 A1 | 10/2020 | Murthy |
| 2020/0385678 A1 | 12/2020 | Murthy et al. |

FOREIGN PATENT DOCUMENTS

| | | |
|---|---|---|
| CN | 105907641 B | 6/2018 |
| EP | 1392814 B1 | 6/2007 |
| EP | 2623587 A1 | 8/2013 |
| JP | 2010/200693 A | 9/2010 |
| WO | 2003/010292 A2 | 2/2003 |
| WO | 2005/113742 A1 | 12/2005 |
| WO | 2009/104296 A1 | 8/2009 |
| WO | 2016/100923 A1 | 6/2016 |
| WO | 2017/004169 A1 | 1/2017 |
| WO | 2017/079674 A1 | 5/2017 |
| WO | 2018/005521 A2 | 1/2018 |
| WO | 2018/041423 A1 | 3/2018 |

OTHER PUBLICATIONS

Fiedler, 1998, Dielectrophorectic Sorting of Particles and Cells in a Microsystem, Analytical Chemistry 70:1909-15.

Fulwyler, 1965, Electronic Separation of Biological Cells by Volume, Science 150(3698):910-11.

International Search Report and Written Opinion issued in International Application No. PCT/US2020/045900, dated Nov. 13, 2020, 21 pages.

Kashaninejad, 2016, Organ-Tumor-on-a-Chip for Chemosensitivity Assay, Micromachines, 7 (130):1-24.

Korin, 2008, Periodic 'Flow-Stop' Perfusion Microchannel Bioreactors for Mammalian and Human Embryonic Stem Cell Long-Term Culture, Biomedical Microdevices, 11(1): 87-94.

Kozbial, 2018, Scale-up of a perfusion-based dendritic cell generation process, Cell & Gene Therapy Insights, 4:1117-1130.

Rosenblatt, 2011, Vaccination with dendritic cell/tumor fusion cells results in cellular and humeral antitumor immune responses in patients with multiple myeloma, Blood, 117(2):393-402.

Rothbauer, 2018, Recent advances in microfluidic technologies for cell-to-cell interaction studies, Lab on a chip, 18:249-270.

Rowjewski, 2013, GMP-Compliant Isolation and Expansion of Bone Marrow-Derived MSCs in the Closed, Automated Device Quantum Cell Expansion System, Cell Transplantation, 22(11):1981-2000.

* cited by examiner

DUTY CYCLE FOR CELL CULTURE SYSTEMS

FIELD OF THE INVENTION

The invention generally relates to cell culture chambers, and specifically to systems and methods for pumping fluids to and from cell culture chambers.

BACKGROUND

Many areas of clinical research and therapy require the isolation, preparation, and expansion of cell lines. In order to replicate desired growth conditions for cells of interest, culture media needs to be controlled for variables such as temperature, gas levels, and concentration of nutrients. Cells can be extremely sensitive to small environmental fluctuations. For example, even a small increase in temperature from 37° C. to 39° C. (i.e., equivalent to a 102° F. fever) can kill certain cells rapidly. A cell culturing process may require several days of incubation, which means an effective cell culture system needs to be able to maintain these precise conditions for long periods of time. Stand-alone cell culture systems can maintain temperature and gas levels, but are expensive and impractical for many labs. An alternative is to grow cells in a cell culture chamber inside a conventional incubator. However, while these arrangements are less costly, they are not as effective for maintaining precise temperature conditions because apparatuses inside the incubator generate heat which cannot be easily dissipated.

SUMMARY

The present disclosure provides automated cell culture systems with pumps configured to operate on a duty cycle, which prevents excess heat generation, thereby allowing the cell culture system to maintain appropriate cell culture temperatures while operating inside a conventional incubator. By producing less heat, systems of the invention reduce the amount of heat that needs to be dissipated, avoiding conditions that would lead to overheating of the system inside the incubator. Whereas in conventional cell culture systems, much heat is generated by the pumping system used to infuse culture medium and remove waste products from cell culture vessels or chambers, in the disclosed systems the pump operates on a duty cycle wherein the pump switches between on and off modes. By running pumps for a short period of time and then shutting them off, less heat is produced.

The present invention recognizes that simply running a standard pump for a short period of time and then turning it off may not be sufficient to deliver nutrients and remove waste effectively. To maintain the overall flow rate, the pump of the present invention operates at a higher flow rate while it is on, to make up for the decreased overall pumping time. However, to emulate static cell culture, and to avoid pulsatile flow which may stimulate certain biological processes and reactions, the disclosed cell culture systems can be operated with a low level of perfusion flow within the range of laminar flow. An optimal duty cycle in which to deliver nutrients and extract waste products at low flow rates may therefore be under 20%, meaning that the pump is on for less than 20% of the time. For example, if the desired overall flow rate is 10 microliters per minute, for a 20% duty cycle the pump delivers 10 microliters within the first 12 seconds (20% of 60 seconds) and is then completely powered off for the next 48 seconds. Thus the overall average flow rate is 10 microliters per minute and the relatively long powered-off time significantly reduces the amount of heat generated over the course of the cycle.

Aspects of the invention involve a cell culture system that includes a cell culture chamber, one or more pumps in fluidic communication with the cell culture chamber, and a processor operably connected to the pump. The processor is configured to operate the pump on recurring duty cycles, each recurrence of the duty cycle comprising an on-cycle and an off-cycle. The off-cycle is longer than the on-cycle. Each recurrence of the duty cycle has the same average flow rate as each other recurrence of the duty cycle.

In embodiments, the cell culture system is sized and configured to fit inside an incubator. The cell culture chamber may include an inlet and an outlet and a fluid reservoir in fluidic communication with the inlet. The pump may be configured to deliver cell culture medium to the cell culture chamber via the inlet and remove waste products from the cell culture chamber via the outlet. During the on-cycle, the pump forces a flow of fluid to and from the cell culture chamber.

In some embodiments, the duty cycle has a duration of about 60 seconds. The on-cycle preferably lasts for under 20% of the duration of the duty cycle. In some embodiments, the average flow rate is less than 1000 µL of fluid per minute.

In related aspects, the invention involves a method for culturing cells. The method includes a first step of providing a cell culture chamber in fluidic communication with a pump and a second step of operating the pump with a processor configured to run recurring duty cycles. Each recurrence of the duty cycle has a same average flow rate and includes an on-cycle in which a fluid flows to and from the cell culture chamber and an off-cycle in which fluid flow is stopped. The off-cycle is longer than the on-cycle.

In some embodiments of the method, the cell culture system is sized and configured to fit inside an incubator. The cell culture chamber may include an inlet and an outlet and a fluid reservoir in fluidic communication with the inlet. In embodiments, operating the pump includes delivering cell culture medium to the cell culture chamber via the inlet and removing waste products from the cell culture chamber via the outlet. During the on-cycle, the pump forces a flow of fluid to and from the cell culture chamber.

In some embodiments, the duty cycle has a duration of about 60 seconds. The on-cycle preferably lasts for under 20% of the duration of the duty cycle. In some embodiments, the average flow rate is less than 1000 µL of fluid per minute.

DETAILED DESCRIPTION

Figure 1A:
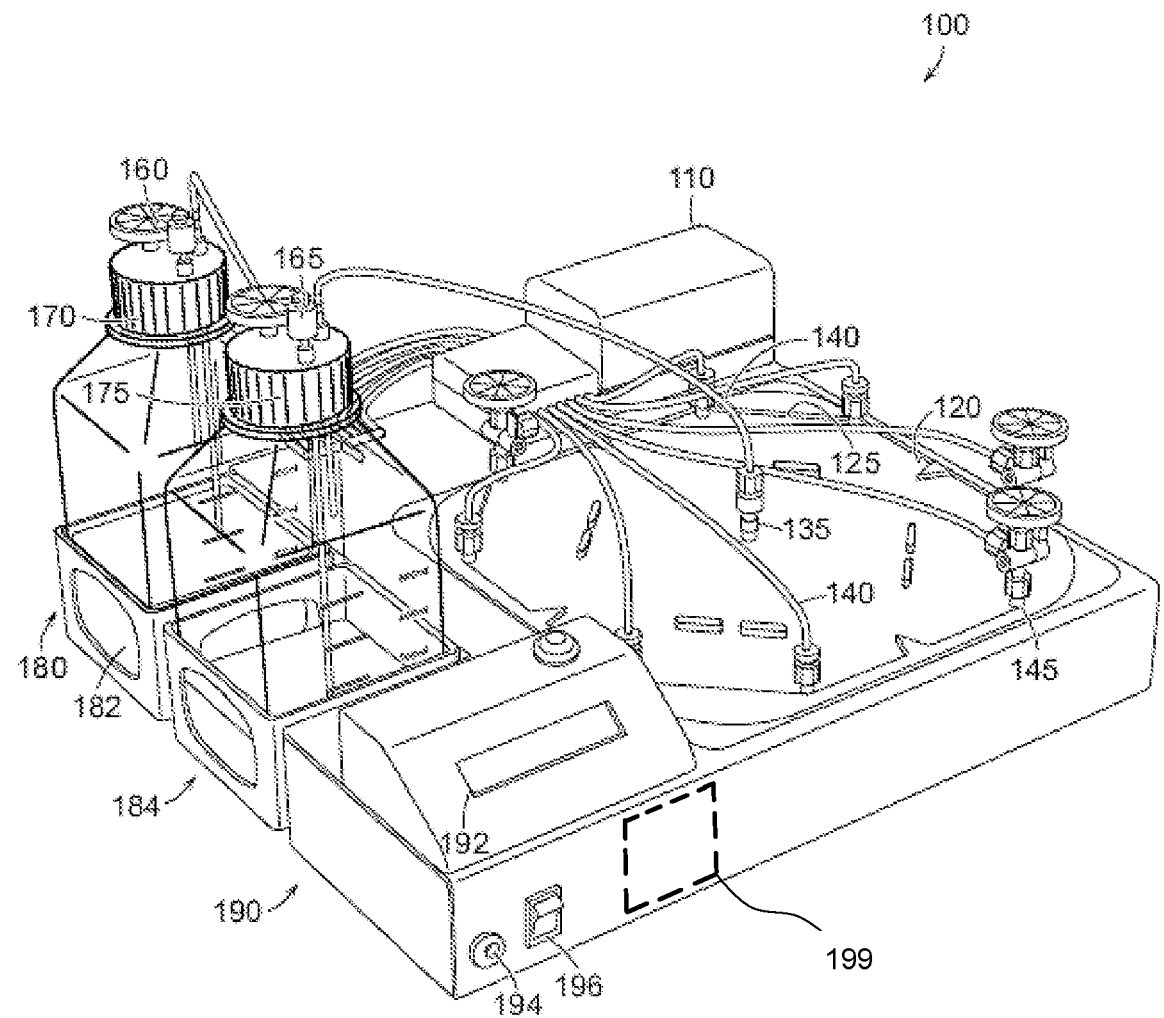
FIGS. 1A and 1B show cell culture systems for use with the invention.

The present disclosure provides cell culture systems that can be used inside conventional incubators and which include pumps configured to run on a duty cycle to effectively maintain fluid flow while avoiding excess heat generation. The disclosed systems and related methods address the challenge for automated cell culture systems that sit inside conventional incubators of needing to dissipate heat. The most common source of heat in an automated cell culture system is the pumping system, which infuses culture medium and removes waste products from cell culture vessels/chambers. Pumping systems according to the present disclosure generate less heat. The disclosed systems and methods are especially useful in perfusion systems where pumps must be run continually over a period of several days. Perfusion systems are highly desirable in automated cell culture because perfusion is a way to not only ensure that cultured cells are exposed to a defined concentration of nutrients but also continual removal of metabolic waste products (unlike static culture where the cells sit in medium that is depleted of nutrients without replenishment along with continual buildup of waste products).

The disclosed system can be used even with cell culture incubators that are not designed to dissipate heat. Such incubators typically operate in room temperature environments where ambient temperature is less than 30° C. The most common desired incubation temperature is physiological temperature, or 37° C. Because heat transfers along gradients of temperature from high temperature to low temperate regions, most incubators only have the ability to heat their interiors, not cool them. Furthermore, many incubators are designed with insulator-like components, such as water jackets, that are designed to retain heat effectively. Given those conditions, the presence of a heat source within conventional incubators will generally cause the interior temperature to rapidly rise. Once this occurs, the temperature control system will shut off heating. However, the insulating features of the incubator will prevent the temperature from decreasing down to desired levels in a timely manner. The present invention solves this problem by operating its pumps on a duty cycle which achieves the desired fluid flow levels while producing much less heat inside the incubator.

A duty cycle is a cycle of operation of a device which operates intermittently rather than continuously. A duty cycle can be defined by an amount of time that the device is on and off over the course of one cycle of operation, or it can be defined by a percentage of the available time that the device is running. Operating one or more pumps in a cell culture system on a duty cycle solves the problems associated with incubators (or any other warm environments). However, while running the pumps for a short period of time and then turning them off reduces heat output, simply running the pumps in a non-continuous manner may not be sufficient to provide desired fluid flows. The flow rate in a duty cycle must be carefully tuned. For one thing, the overall flow rate must be sufficient to deliver nutrients and remove waste effectively. But pulsatile flow is analogous to the natural pulsing rhythm within the human body, and many cell types are sensitive to this. Pulsatile flow may cause certain biological processes and reactions to occur, or it may cause shearing in many cell types having increased shear sensitivity. Therefore in a desire to closely emulate static culture that is widely used in biological research settings, it is desirable to operate the cell culture systems with a low level of perfusion flow. Low in this context can mean fluid flow that is well within the regime of laminar flow (wall shear stress levels well below physiological levels of 15 dynes per $cm^2$) and typically in magnitudes of under 1000 µL per minute. In some embodiments, the average flow is under 100 µL per minute. In other embodiments, the average flow is under 10 µL per minute.

An optimal duty cycle for use with the present invention in which to deliver nutrients and extract waste products at low flow rates is for the pump or pumps to operate for less than 20% of the available time. For example, if the desired overall flow rate is 10 microliters per minute, for a 20% duty cycle then the pump delivers 10 microliters within the first 12 seconds (20% of 60 seconds) and is then completely powered off for the next 48 seconds. Thus the overall average flow rate is still 10 microliters per minute and the relatively long off time significantly reduces the amount of heat generated. In conventional incubators, if heat generation from an instrument is maintained at under 2 Watts, undesirable temperature rise can be avoided.

In other embodiments, the duty cycle can be about 1%, about 2%, about 5%, about 10%, about 25%, about 30%, about 40%, about 50%, or greater. The duration of the duty cycle is preferably about one minute, but in various embodiments can be about 1 second, about 2 seconds, about 5 second, about 10 seconds, about 15 seconds, about 20 seconds, about 30 seconds, about 45 seconds, about 90 seconds, about 2 minutes, about 3 minutes, about 4 minutes, about 5 minutes, about 10 minutes, about 20 minutes, or longer. The average flow rate over the course of the duty cycle is generally under 1000 µL per minute. In embodiments, it is under 100 µL per minute, or under 10 µL per minute.

Operating one or more pumps on a duty cycle is useful for a variety of different cell culture systems and setups. Several embodiments of the cell culture systems employing duty cycles to control pump activity according to the present disclosure are described below and shown in the figures.

FIG. 1A shows an embodiment of a system 100 for generating dendritic cells. A peristaltic pump 110 is provided. The pump 110 is used to pump fluid into and out of the cell culture cartridge 120. The pump 110 is operably connected to a processor 199 configured to receive from a memory instructions to operate the pump 110 in a duty cycle as described herein. The instructions specify a duration of the duty cycle, as well as a duration of the on-cycle in which the pump is on and a duration of the off-cycle in which the pump is off. The on-cycle and/or off-cycle can be defined as an amount of time or as a percentage of available time in the duty cycle. In general, the duty cycle repeats on a continuous loop, such that when one duty cycle ends, another begins, which has the effect of intermittently turning the pump 110 on and off.

The cell culture cartridge 120 has a bottom surface 125 to which cells adhere. In other embodiments, cells do not adhere to the bottom surface. The cell culture cartridge 120 has eight fluid inlets 145 arranged at the corners of the cell culture cartridge 120. One fluid outlet 135 is arranged at a center of the cell culture cartridge 120. Connective tubing 140 connects the fluid inlets with the differentiation medium reservoir (perfusion source) 180 containing differentiation medium 182. The differentiation medium reservoir 180 contains differentiation medium 182 that will be pumped into the cell culture cartridge 120. The connective tubing 140 also connects the fluid outlet 135 with the waste reservoir 184. Depleted medium will be pumped out of the cell culture cartridge 120 through the outlet 135 and into the waste reservoir 184. Lids 170 and 175 on the differentiation medium reservoir 180 and the waste reservoir 184 are not removable, thereby maintaining a sterile system. In other embodiments, the lids 170 and 175 are removable. Stopcocks and/or LAVs 160 and 165 on the reservoir bottles 180 and 184 allow for sterile transfer of differentiation medium to fill the inlet bottle and remove waste from the outlet bottle. The console 190 provides designated spaces for arrangement of the previously mentioned components and also provides a display/userface 192, connection 194, and on/off switch 196.

Figure 1B:
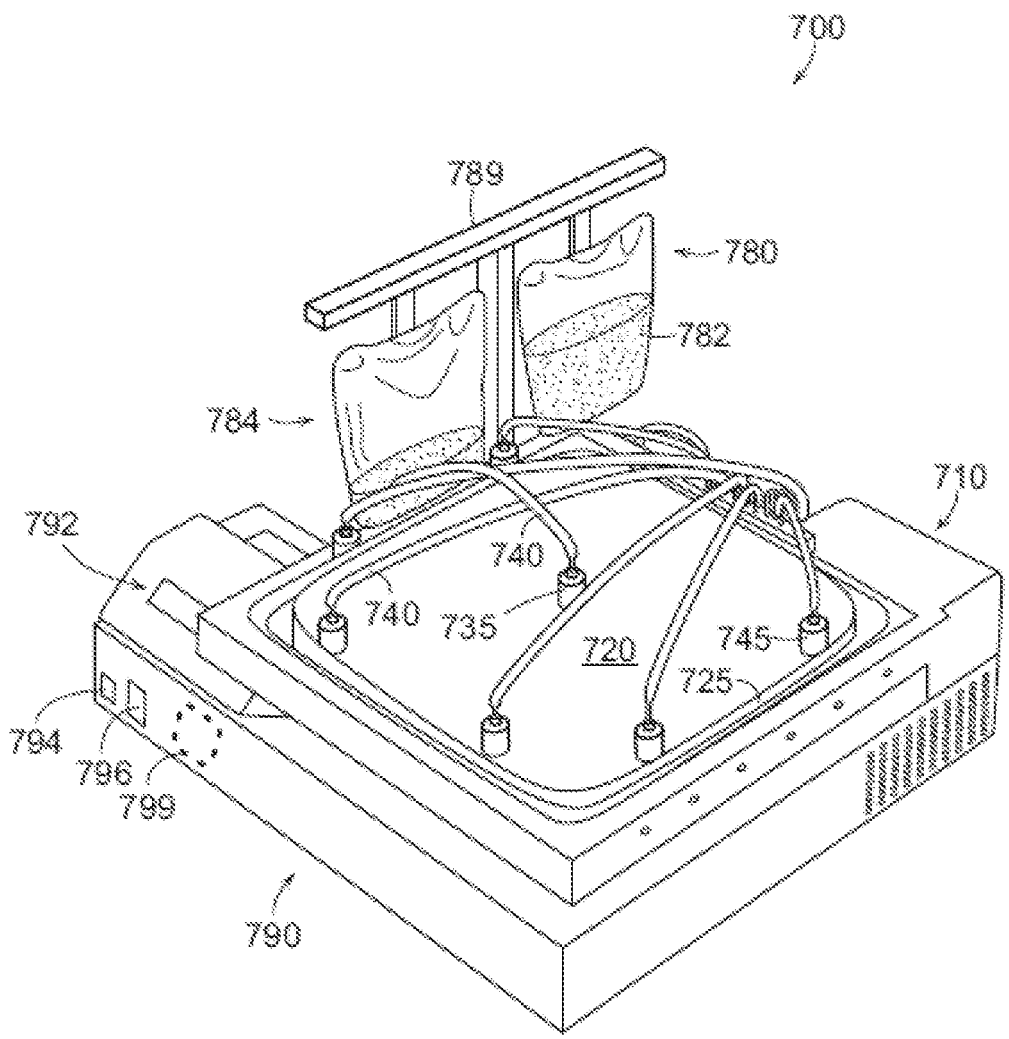

FIG. 1B shows another embodiment of a system 700 for generating dendritic cells. A peristaltic pump 710 is provided. The pump 710 is used to pump fluid into and out of the cell culture cartridge 720. The pump 710 is operably connected to a processor 799 configured to receive from a memory instructions to operate the pump 710 in a duty cycle as described herein. The instructions specify a duration of the duty cycle, as well as a duration of the on-cycle in which the pump is on and a duration of the off-cycle in which the pump is off. The on-cycle and/or off-cycle can be defined as an amount of time or as a percentage of available time in the duty cycle. In general, the duty cycle repeats on a continuous loop, such that when one duty cycle ends, another begins, which has the effect of intermittently turning the pump 710 on and off.

The cell culture cartridge 720 has a bottom surface 725 to which cells adhere. In other embodiments, cells do not adhere to the bottom surface. The cell culture cartridge 720 has eight fluid inlets 745 arranged at the corners of the cell culture cartridge 720. One fluid outlet 735 is arranged at a center of the cell culture cartridge 720. Connective tubing 740 connects the fluid inlets with the differentiation medium reservoir (perfusion source) 780 containing differentiation medium 782. The differentiation medium reservoir 780 is in the form of a sterile bag containing differentiation medium 782 that will be pumped into the cell culture cartridge 720. The connective tubing 740 also connects the fluid outlet 735 with the waste reservoir 784, which is another bag. The differentiation medium reservoir 780 and the waste reservoir 784 are supported by pole 789. Depleted medium will be pumped out of the cell culture cartridge 720 through the outlet 735 and into the waste reservoir 784. The console 790 provides designated spaces for arrangement of the previously mentioned components and also provides a display/userface 792, connection 794, and on/off switch 796.

System 100 is shown with a single pump, but it is to be understood that cell culture systems of the present invention can have more than one pump. For example, one pump may be configured to pump fluid from the reservoir 180, while another pump may be configured to pump waste away from the cell culture cartridge into waste reservoir 184. In embodiments having more than one pump, each pump may be connected to the same processor or different processors, each configured to run its respective pump on a duty cycle, which may have the same or different parameters from each other.

The system 100 is sized and configured to be placed inside of a conventional incubator, where it can operate for a period of time sufficient to generate the desired population of dendritic cells. The pump or pumps function according to the processor instructions on a duty cycle, which provides desirable fluid flow conditions and prevents overheating of the system. Additional features and configurations of systems for generating dendritic cells that are compatible with the present disclosure are described in U.S. application Ser. No. 16/192,062, filed Nov. 15, 2018, the contents of which are incorporated by reference herein.

In certain embodiments, one or more pumps are operably coupled to the cell culture chamber for perfusing perfusion medium into the cell culture chamber. Perfusion medium comprises any suitable medium. In some embodiments, the perfusion medium is differentiation medium. The cell culture cartridge can also include one or more fluid reservoirs. The fluid reservoirs are in fluidic communication with the cell culture chamber and can be operably coupled to one or more pumps. One or more tubes for connecting the fluid reservoirs to the pumps and cell culture chamber are also provided. In certain aspects, the one or more pumps are configured for pumping fluid from the fluid reservoir, through the cell culture chamber, and into the waste collection reservoir. The one or more pumps are operably connected to a processor which turns the one or more pumps on and off over the course of a duty cycle. The parameters of the duty cycles are defined by a set of instructions stored in a memory in communication with the processor. Processors, memories, and computer configurations are described in more detail below. In an embodiment, fluid moves from the fluid reservoir, through tubing to the pump and into the cell culture chamber via inlet, back out of the cell culture chamber via outlet, through tubing, and into the waste collection reservoir.

In certain embodiments, the fluid reservoir and/or waste collection reservoir can each be provided as one or more capped bottles either contained within the cell culture chamber or fluidically coupled to the chamber. Each reservoir contains an inlet port and an outlet port, or an outlet port and a vent fluidically coupled to the inlet of one or more cell culture chambers. In certain aspects, for example, Luer connectors and silicone gaskets cut to fit around the Luer connectors can be used to prevent leakage through either or both of the inlet or outlet.

In certain embodiments, the one or more cell culture cartridges are sized and configured to fit within an incubator, such that the process will be carried out within an incubator. Conditions within the incubator include sustained temperatures of 37° C. and 95-100% relative humidity. Thus, the materials chosen must have the integrity to withstand these conditions, given that the materials (including fluids and biologics) tend to expand under such conditions. Furthermore, in some circumstances, conditions within the incubator remain stable, and automated recording of the temperature is possible to have knowledge of temperature fluctuations to correlate with any aberrations in the reactions performed in the incubator. In accordance with the present disclosures, any power supply and pumps are configured to not change the environment within the incubator because the duty cycle prevents them from generating excessive heat.

Accordingly, in one embodiment, the pumps are housed separately from the cell culture cartridge, but are still in fluidic and operable communications with the cell culture cartridge. In another embodiment, the pumps are directly attached to the cell culture cartridge. In all embodiments the pumps are configured to be located within the incubator. The duty cycle operation of the pumps is sufficient on its own to prevent overheating, but in some embodiments the system may be operably connected to a heat sink and/or a fan for additional heat dissipation. Regardless of the configuration, the pumps are operably coupled to a processor for running the duty cycle and the pumps are also operably coupled to the cell culture cartridge, and, in turn, the cell culture chambers. Additional details regarding perfusion based automated cell culture systems, such as small scale culture system for endothelial cell culture with on-board reagent storage and perfusion enabled by an on-board disposable peristaltic pump and a larger scale culture system for dendritic cell generation from monocytes using chambers with polystyrene bottom surfaces, can be found in US 2018/

0171296; US20180251723; and WO 2018/005521; each of which is incorporated herein by reference in its entirety.

In still other aspects, the cell culture chamber includes one or more sensors operably coupled to the cell culture chamber. The sensors may be capable of measuring any suitable parameters. For example, the sensors may be capable of measuring one or more parameters within the cell culture chamber, such as pH, dissolved oxygen, total biomass, cell diameter, glucose concentration, lactate concentration, and cell metabolite concentration. In embodiments wherein the system includes multiple cell culture chambers, one or more sensors can be coupled to one or more of the cell culture chambers. In certain embodiments, one or more sensors are coupled to one or more cell culture chambers, but not all of the chambers in a system. In other embodiments, one or more sensors are coupled to all of the cell culture chambers in a system. In systems having multiple chambers operably coupled to one or more sensors, the sensors can be the same in each of the chambers to which they are coupled, they can all be different, or some sensors can be the same and some can be different. In certain aspects, the one or more sensors are operably coupled to a computer system having a central processing unit for carrying out instructions, such that automatic monitoring and adjustment of parameters is possible. Additional details regarding computer systems for implementing methods of the present invention using the cell culture chambers is provided below.

In some embodiments, one or more sensors can measure the temperature within one or more cell culture chambers, fluid reservoirs, tubing, and/or in the incubator generally. The temperature sensor can provide feedback to the processor that controls the duty cycle, indicating whether the on-cycle should increase or decrease to fine tune the temperature in the system. If the sensor detects that the temperature in of the cell culture is getting to high, the duty cycle can adjust so that the pumps are on for a shorter period of time to generate less heat. If the on-cycle is shortened, the pumps will generally increase in fluid flow so that the average fluid flow over the course of the duty cycle remains the same.

In certain embodiments, the cell culture chamber has an inlet and an outlet, both of which can be used to fluidically couple the chamber via a fluidic connector with one or more additional vessels. In certain embodiments the additional vessels include one or more additional cell culture chambers. Systems of the present invention can include, for example, 2, 3, 4, 5, 6, 7, 8, 9, 10, 15, 20, 30, 40, 50, 60, 70, 80, 90, 100, or any number of cell culture chambers in between or higher than one hundred configured to fluidically connect with one another in a series to produce the immunotherapeutic product. Alternatively or additionally, one or more cell culture chambers can be arranged in parallel with one another to allow for production of immunotherapeutic product for more than one individual at a time. In a preferred embodiment, the cell culture chambers of the cell culture cartridge are connected via a sterile connection.

In one embodiment, a perfusion of medium and cytokines can be provided to the cellular mixture within the cell culture chamber(s) to assist with the formation of the cell-based immunotherapeutic product. In plate-based protocols for stimulation of T cells by DCs, a culture volume of approximately 2 mL is maintained from the start, with infusion of cytokines occurring twice within each 7 day stimulation period. A major advantage of perfusion is the ability to maintain consistent local concentration profile of medium and cytokines, which ensures greater yields and the potential ability to speed up the process of monocyte differentiation to DCs compared to prior art plate-based protocols. However, the combination of adherent (DC) and non-adherent (T cell) types, along with the high sensitivity of DCs to mechanical forces poses challenges to the stimulation and expansion of antigen-specific T-cells, especially with respect to the flow of fluid through the cell culture chamber. Thus, in those embodiments in which medium and cytokines are provided via perfusion, systems of the present invention must be able to supply cells with nutrients and cytokines without removing cells from the cell culture cartridge while also taking into account the shear sensitivity of certain antigen-presenting cells, such as DCs. Essentially, some embodiment systems and methods of the invention aim to optimize retention of autocrine/paracrine signals favoring T cell proliferation while refreshing growth factors and maintaining minimal physical stimulation of DCs. In order to account for this, both the direction and the rate of perfusion flow through the cell culture chamber must be taken into consideration. For example, some embodiments of the invention may comprise medium flow arrangement other than unidirectional flow, such as counter-current medium flow arrangement.

In embodiments, a cell culture system is provided that includes a cell culture chamber and a central processing unit comprising memory containing instructions executable by the central processing unit. In certain aspects, the instructions cause the system to receive as a first input data comprising a size of the cell culture chamber, receive as a second input data comprising a first concentration of a first cell type and a second concentration of a second cell type in one or more fluids that will be introduced into the cell culture chamber, and calculate, based on the first and second inputs, a perfusion rate of a perfusion fluid that will be introduced into the cell culture chamber that maximizes a probability of the first cell type and the second cell type contacting each other within the cell culture chamber. The system may further calculate the desired duty cycle parameters (e.g., duration of the duty cycle, percentage of time for the on-cycle, and flow rate during the on-cycle) based on the desired average flow rate, the heat output of the system, and the desired cell culture temperature inside the incubator. The system also includes one or more pumps operably coupled to one or more perfusion fluid reservoirs and operably coupled to the central processing unit, such that the central processing unit also controls the perfusion rate of the perfusion fluid by running the duty cycle to control the one or more pumps.

Systems of the invention can also include or be operably coupled to one or more control systems for controlling the movement of fluid through the system; monitoring and controlling various parameters, such as temperature, within the systems; as well as detecting the presence of cell-based immunotherapeutic products, quantity of product (directly or indirectly), conversion rate, etc. The system may also be equipped with numerous classes of software, such as an advanced real-time process monitoring and control process, allowing for feedback control, as well as processes that allow integration and scale-up given reaction and purification results obtained using the system.

Figure 2A:
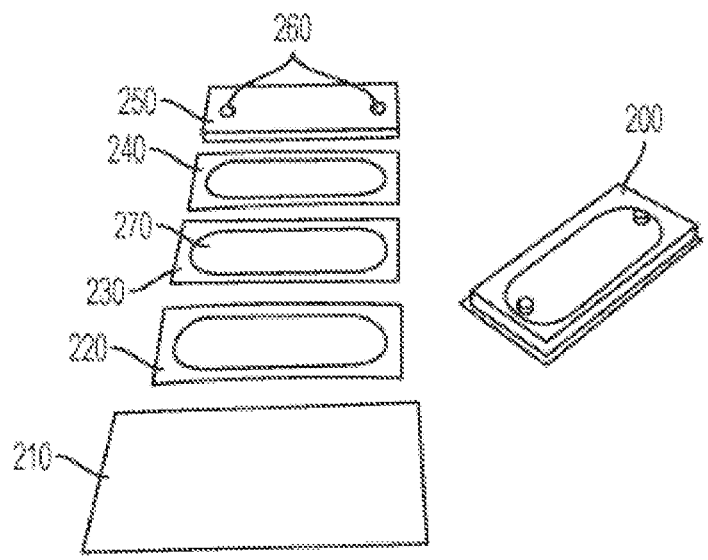
FIGS. 2A and 2B show cell differentiation cassettes.
Figure 2B:
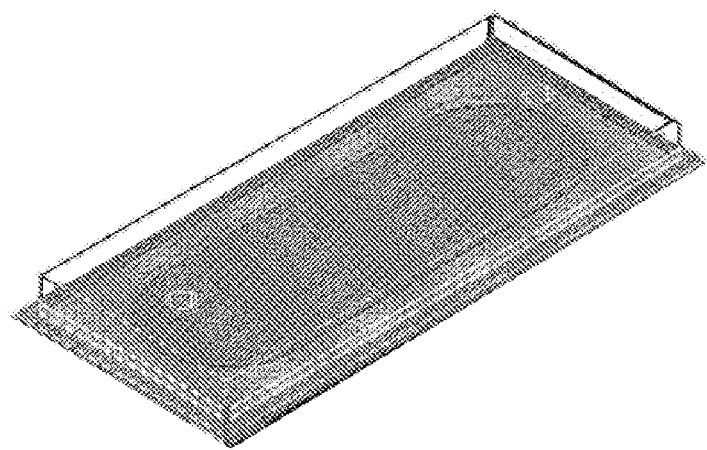
Figure 3:
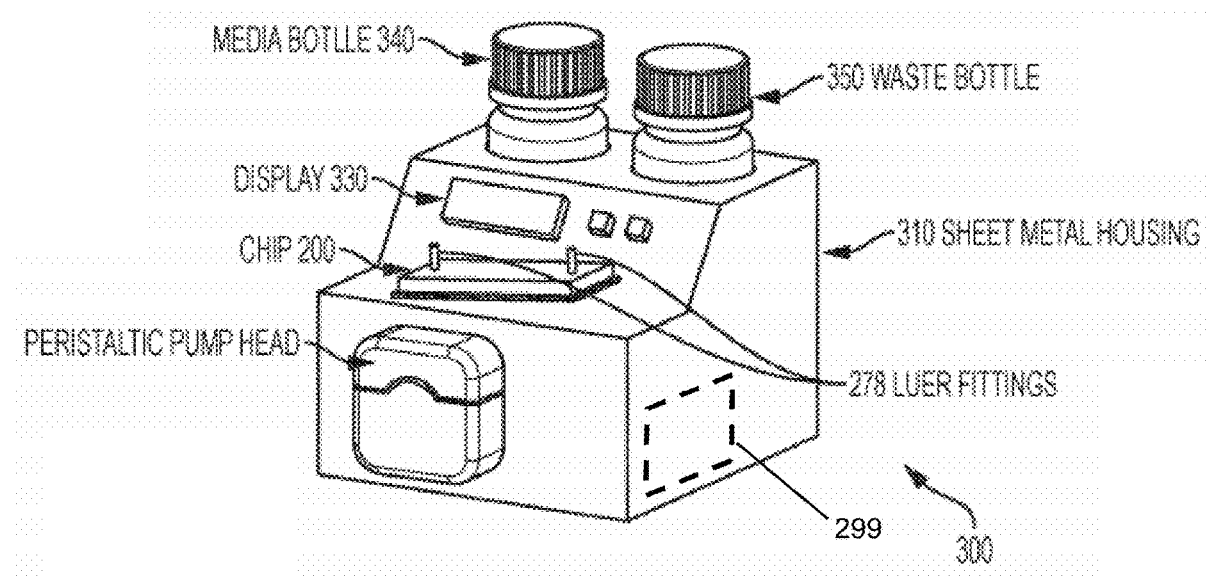
FIG. 3 shows a cell culture system using the cell differentiation cassettes of FIGS. 2A and 2B.

Systems for automated production of dendritic cells from monocytes (MCs) obtained from peripheral blood are shown in FIGS. 2A-B and 3. The described systems can incorporate the disclosed duty cycle pump operation to allow the systems to be used inside a standard incubator.

FIGS. 2A-2B show a design of a dendritic cell differentiation cassette compatible with the present invention. Cassette 200 is built from the layers shown at the left side of FIG. 2A, which are assembled with the aid of double sided adhesive film. The design of the cassette allows it to receive a suitable volume of whole blood or another fluid sample containing MCs, bind essentially all of the MCs contained in the sample. The cassette contains a cell culture chamber which forms the central open fluid space within the cassette. The floor of the chamber is, or contains as a portion thereof, a MC binding surface. The preferred geometry of the cell culture chamber is that of a flat, thin, space whose inner sides are all rounded and devoid of corners or vertices. An oval or rounded rectangular profile of the chamber is preferred. The flat surface and low height help to avoid turbulence that would lead to fluid shear stress, which would be disruptive to cells within the chamber and can reduce both cell viability and yield. Therefore, an important feature of the cassette is that it avoids or minimizes exposure of the cells within to shear stress. This is accomplished by the use of a flat surface with a minimum of protuberances or surface roughness, by the avoidance of sharp boundaries within the fluid pathway and within the cell culture chamber, by the use of laminar flow where possible (which is enhanced by keeping the cell culture chamber thin, such as from about 0.1 mm to about 2 mm in height), and by the inclusion of a bubble trap or gas venting mechanism for the elimination of gas bubbles during perfusion of the cell culture chamber. Both the achievement of laminar flow and the elimination of gas bubbles are promoted by the positioning of inlet and outlet ports at opposite sides of the cell growth chamber, such as shown in FIG. 2A. Further, the cassette can be mounted at an angle, with the outlet port positioned above the level of the inlet port, to assure that any bubbles entering the cell growth chamber through the inlet port are quickly eliminated at the outlet port by rising up to the outlet port, aided by their buoyancy.

Fluidic devices of the invention, including the dendritic cell differentiation cassette, or any cell growth or culture chamber, can be provided in either a microfluidic embodiment (i.e., wherein one or more channels or chambers therein has a dimension in the range of from about 1 μm to about 999 μm) or a macrofluidic embodiment (wherein all of the channels or chambers therein have dimensions of about 1 mm or more. The fluidic devices can further include fluid reservoirs, additional fluid channels or compartments, gaskets or seals, mixing zones, valves, pumps, vents, channels for pressurized gas, electrical conductors, reagents, ports, and tubing as required by a particular design. They also may contain one or more control modules, transmitters, receivers, processors, memory chips, batteries, displays, buttons, controls, motors, pneumatic actuators, antennas, electrical connectors, and the like. The devices preferably contain only materials that are nontoxic to mammalian cells and that are compatible with sterilization by the use of alcohol and/or heat. Where needed, surfaces of the devices can be made more hydrophilic, such as by exposure to a plasma, or can be coated with one or more gels, chemical functionalization coatings, proteins, antibodies, glycoproteins, lipids, glycolipids, nucleic acids, proteoglycans, glycosaminoglycans, cytokines, or cells. The devices are also preferably compatible with use within a standard mammalian cell culture incubator, and in some embodiments do not allow the diffusion of gas through the material, as that could alter the composition of the culture medium within the device. Fluidic devices of the invention also are preferably modular and capable of fluidic connection to other similar devices either in series (i.e., with fluid flowing from one device into another) or in parallel, and may also be so configured as to physically stack with one another or be capable of physical arrangement within a related device such as an incubator, a pump, or a dendritic cell generation system. Fluidic devices of the invention are preferably devoid of fluid leaks under operating conditions and capable of sterile operation over a period of days to weeks. Other configurations of dendritic cell differentiation cassettes are also contemplated, and are described in further detail in US 2018/0171296, the contents of which are incorporated by reference herein.

A dendritic cell generation system employing the cassettes of FIGS. 2A-2B includes at least a cell culture chamber, a pump, a culture medium reservoir, and fluidic connections between the medium reservoir, the pump, and the cell culture chamber. The system includes a processor operably connected to the pump for executing instructions for running the pump on a duty cycle as described herein.

The system can also be provided without the cell culture chamber, which can be added to the system by the user, optionally together with one or more tubings for connecting the culture medium reservoir to the pump and DC differentiation cassette. The cell culture chamber can be provided as part of one or more dendritic cell differentiation cassettes as described above, or as one or more different structures. The culture medium reservoir can be provided as one or more capped bottles, each containing an inlet port and an outlet port, or an outlet port and a vent a fluidically coupled to the fluid inlet port of the one or more dendritic cell differentiation cassettes; a fluid collection reservoir fluidically coupled to the fluid outlet port of the one or more dendritic cell differentiation cassettes; and a pump configured for pumping fluid from the culture medium reservoir, through the cell culture chamber of the one or more dendritic cell differentiation cassettes, and into the fluid collection reservoir.

An embodiment of a DC generating system 300 is depicted in FIG. 3. The system includes housing 310 with spaces for containing culture medium reservoir 340 and waste reservoir 350 (each the size and shape of commercially available glass or plastic culture medium bottles with plastic caps), a mounting area for DC differentiation cassette 200, an exposed peristaltic pump head configured for accepting peristaltic pump tubing leading from the culture medium bottle to the inlet port of the cassette (another tubing leading from the outlet port of the cassette to the waste bottle does not need to pass through the pump head), a display 330, and control buttons, knobs, or switches. The pump is controlled by a processor 299 configured to run the pump on a duty cycle.

The system 300 is sized and configured to be positioned and operated within a conventional incubator Similar systems that include two or more cassettes and pump heads (e.g., one for each cassette, such as 2, 3, 4, 5, 6, 7, 8, 9, 10, or more cassettes and pump heads) are also contemplated. In such multi-cassette systems, the processor, control electronics, display, and buttons, knobs, or switches can either be shared among the different cassettes, or duplicated with one set for each cassette.

Figure 4:
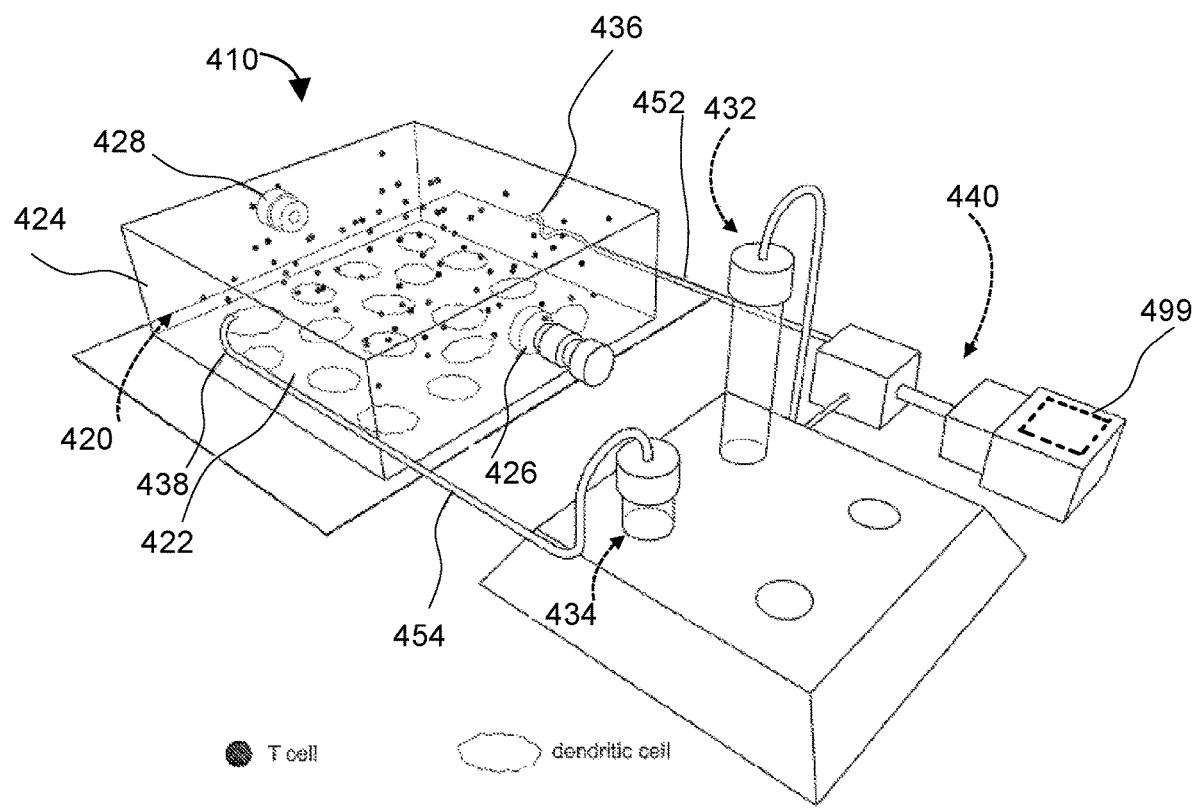
FIG. 4 shows a system of the invention with one cell culture chamber.

In another example embodiment, as shown in FIG. 4, a biological reactor 410 is provided including a cell culture chamber 420 that includes a bottom surface 422 and at least one additional surface 424. The bottom surface 422 is comprised of a first material to which cells adhere, wherein the at least one additional surface 424 is comprised of a second material that is gas permeable. The cell culture chamber also comprises one or more inlets 426, 436 and one or more outlets 428, 438. In certain embodiments, the biological reactor also includes at least one perfusion fluid reservoir 432, at least one waste fluid reservoir 434, at least one pump 440 for moving perfusion fluid through the chamber 420, as well as associated inlets 436 and outlets 438 for transporting fluid to and from the reservoirs 432, 434 and through the chamber 420. The bioreactors 410 will also include one or more pumps 440 operably coupled to the cell culture chamber 420 for perfusing perfusion medium into the cell culture chamber. The bioreactors 410 can also include one or more fluid reservoirs 432. The fluid reservoirs 432 are in fluidic communication with the cell culture chamber 410 and can be operably coupled to one or more pumps 440. One or more tubes for connecting the fluid reservoirs to the pumps and cell culture chamber are also provided. In certain aspects, the one or more pumps are configured for pumping fluid from the fluid reservoir, through the cell culture chamber, and into the waste collection reservoir. In the example embodiment shown in FIG. 4, fluid moves from the fluid reservoir 432, through tubing 452 to the pump 440 and into the cell culture chamber 420 via inlet 436, back out of the cell culture chamber 420 via outlet 438, through tubing 454, and into the waste collection reservoir 434. The one or more pumps are connected to a processor 499 that runs the pumps on a duty cycle as disclosed herein.

The inlets and outlets of reactor 410 can be used to fluidically couple the chamber via a fluidic connector with one or more additional vessels. In certain embodiments the additional vessels include one or more additional cell culture chambers, as will be described in more detail below. Systems of the present invention can include, for example, 2, 3, 4, 5, 6, 7, 8, 9, 10, 15, 20, 30, 40, 50, 60, 70, 80, 90, 100, or any number of cell culture chambers in between or higher than one hundred configured to fluidically connect with one another in a series to produce the immunotherapeutic product. Alternatively or additionally, one or more cell culture chambers can be arranged in parallel with one another to allow for production of immunotherapeutic product for more than one individual at a time. In a preferred embodiment, the cell culture chambers of the bioreactors are connected via a sterile connection.

Figure 5C:
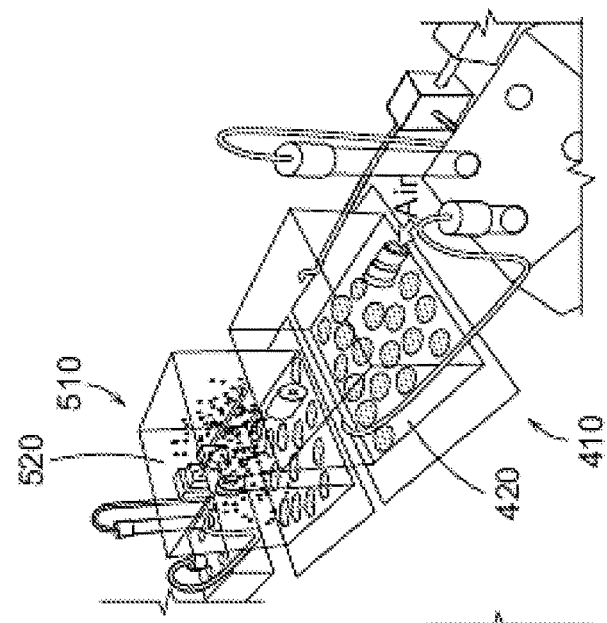
FIG. 5 shows a process for connecting cell culture chambers and transferring fluid between them.
Figure 5B:
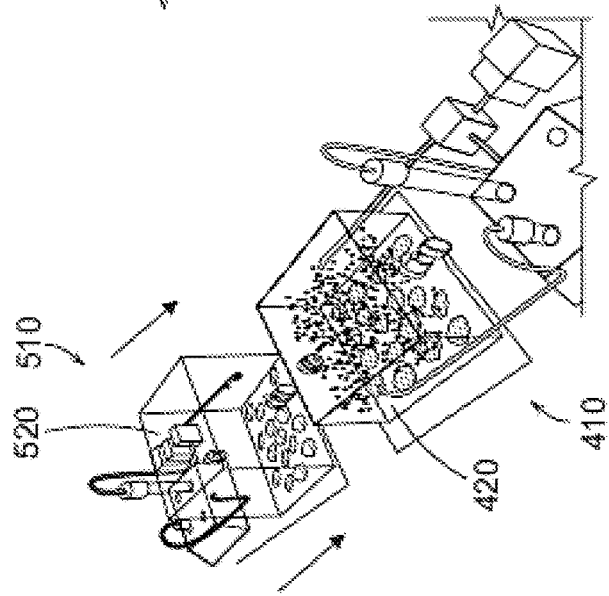
Figure 5A:
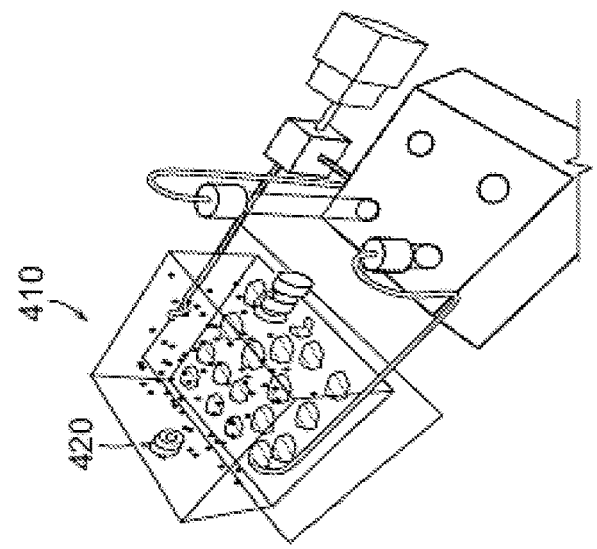

An example configuration of a multi-bioreactor system can be found in FIG. 5, panels B and C, with additional detail regarding the processes carried out using this configuration provided below. As shown in FIG. 5, in the event that a second bioreactor 510 is involved, the second cell culture chamber 520 is moved into position to connect with the first cell culture chamber 420 chamber via the outlet of the first chamber and the inlet of the second chamber. The connection is preferably a sterile connection. The connection allows for the injection of sterile air into the first cell culture chamber 420 to transfer the supernatant containing the expanded T-cells into the second cell culture chamber 520. Alternative techniques known in the art of fluid flow may be employed to transfer the supernatant from the first cell culture chamber 420 to the second cell culture chamber 520.

As also shown, each bioreactor includes its own fluid and waste collection reservoirs, pumps, and associated tubing. However, it is to be understood that the reservoirs and pumps can be shared between bioreactors. The pumps can be connected to the same processor or different processors for controlling their duty cycles.

In certain embodiments, there is a 1:1 ratio of cell culture inlets to cell culture outlets, such as when the one or more biological reactors are arranged in series with one another, as shown in FIG. 5. In other embodiments, the ratio of outlets to inlets for at least a portion of biological reactors is 1:2. For example, the outlet of one cell culture chamber 420 can be fluidically connected to the inlet of two cell culture chambers (not shown) such that fluid flowing out of the first cell culture chamber 420 is split into two streams, sending one stream into a second cell culture chamber and second stream into a third cell culture chamber. In this configuration, both the second and the third cell culture chambers can be used to further stimulate and expand the T-cells. Additionally, or alternatively, one of the second or third cell culture chambers can be configured to allow for the monitoring of reaction and flow parameters using one or more sensors (for measuring temperature, for example) operably coupled to the chamber. In this way, one of the chambers remains free from additional sensors, some of which may need to penetrate the walls of the cell culture chamber, which can add to the risk of leakage and/or contamination.

Figure 6:
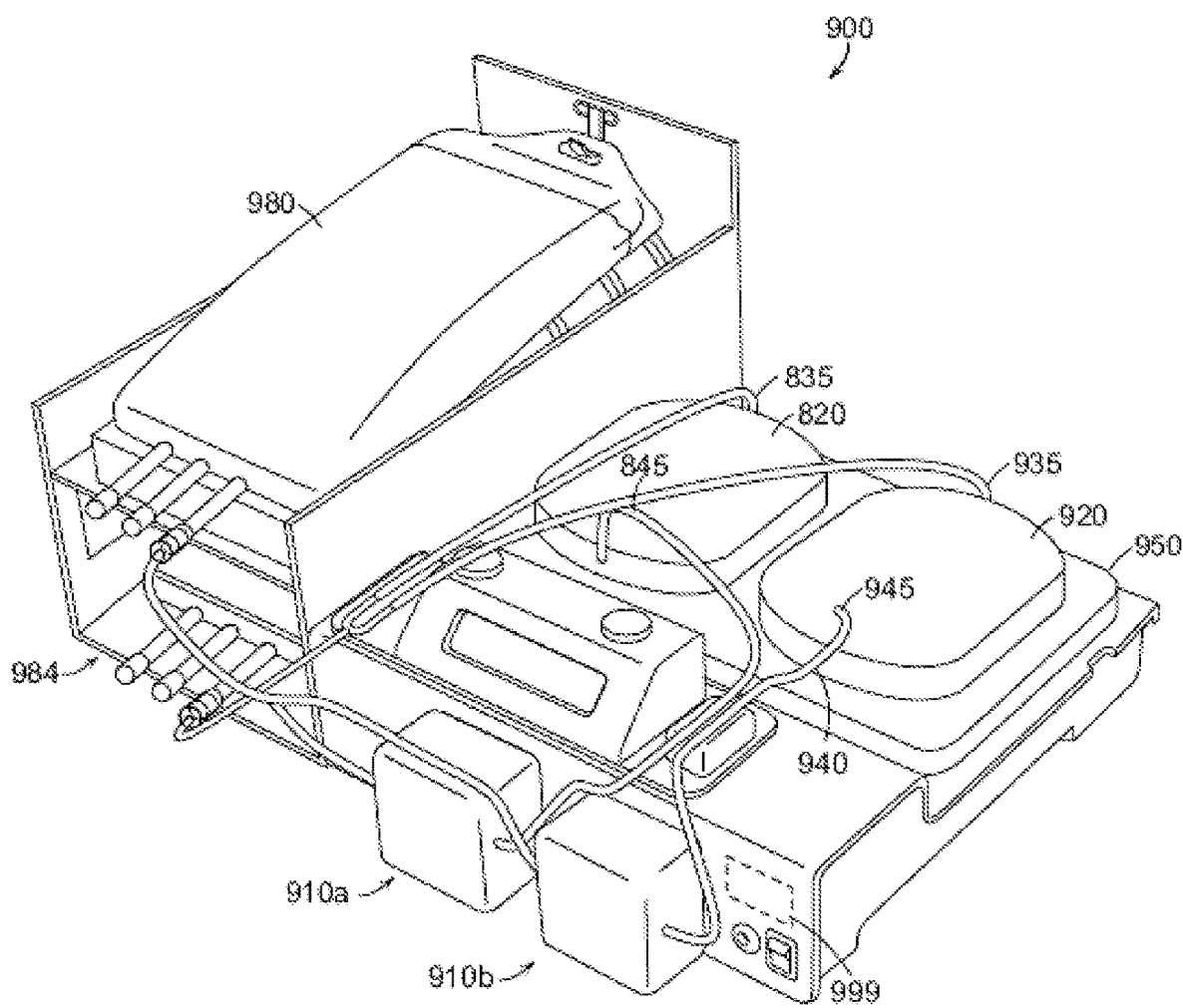
FIG. 6 shows a system of the invention with multiple cell culture chambers.

FIG. 6 shows another example of a multi-bioreactor system 900. The system 900 includes a first cell culture chamber 820 and a second cell culture chamber 920, which have inlets 845 and 945 connected to tubing 940 in fluid communication with a fluid reservoir 980. The cell culture chambers have outlets 835 and 935 in fluid communication with waste reservoir 984. Pumps 910*a* and 910*b* facilitation pumping of fluid from the fluid reservoir 980 to the cell culture chambers 820 and 920. The pumps are controlled by processor 999, which runs a duty cycle as described herein.

In certain embodiments, the one or more biological reactors can be provided in a system containing modules for effectuating various other processes prior to, concurrent with, or subsequent to the process occurring within the cell culture chambers of the biological reactors. Other configurations of multi-bioreactor systems are also contemplated, and are described in further detail in WO 2018/005521, the contents of which are incorporated by reference herein As has been described with respect to the various embodiments disclosed herein, systems and methods involve computer components such as a memory for storing instructions related to duty cycle and a processor for executing the instructions to thereby control the pumps. Aspects of the present disclosure described herein, such as control of the movement of fluid through the system, as described above, and the monitoring and controlling of various parameters, can be performed using any type of computing device, such as a computer or programmable logic controller (PLC), that includes a processor, e.g., a central processing unit, or any combination of computing devices where each device performs at least part of the process or method. In some embodiments, systems and methods described herein may be performed with a handheld device, e.g., a smart tablet, a smart phone, or a specialty device produced for the system.

Methods of the present disclosure can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. Elements of computer are a processor for executing instructions and one or more memory devices for storing instructions and data.

Generally, a computer will also include, or be operatively coupled to receive data from or transfer data to, or both, one or more non-transitory mass storage devices for storing data, e.g., magnetic, magneto-optical disks, or optical disks. In some embodiments, sensors on the system send process data via Bluetooth to a central data collection unit located outside of an incubator. In some embodiments, data is sent directly to the cloud rather than to physical storage devices. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and frontend components. The components of the system can be interconnected through network by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to embodiments of the invention involves transforming a tangible, non-transitory, computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines employed in embodiments of the invention may include one or more processors (e.g., a central processing unit (CPU) a graphics processing unit (GPU) or both), a main memory and a static memory, which communicate with each other via a bus.

Figure 7:
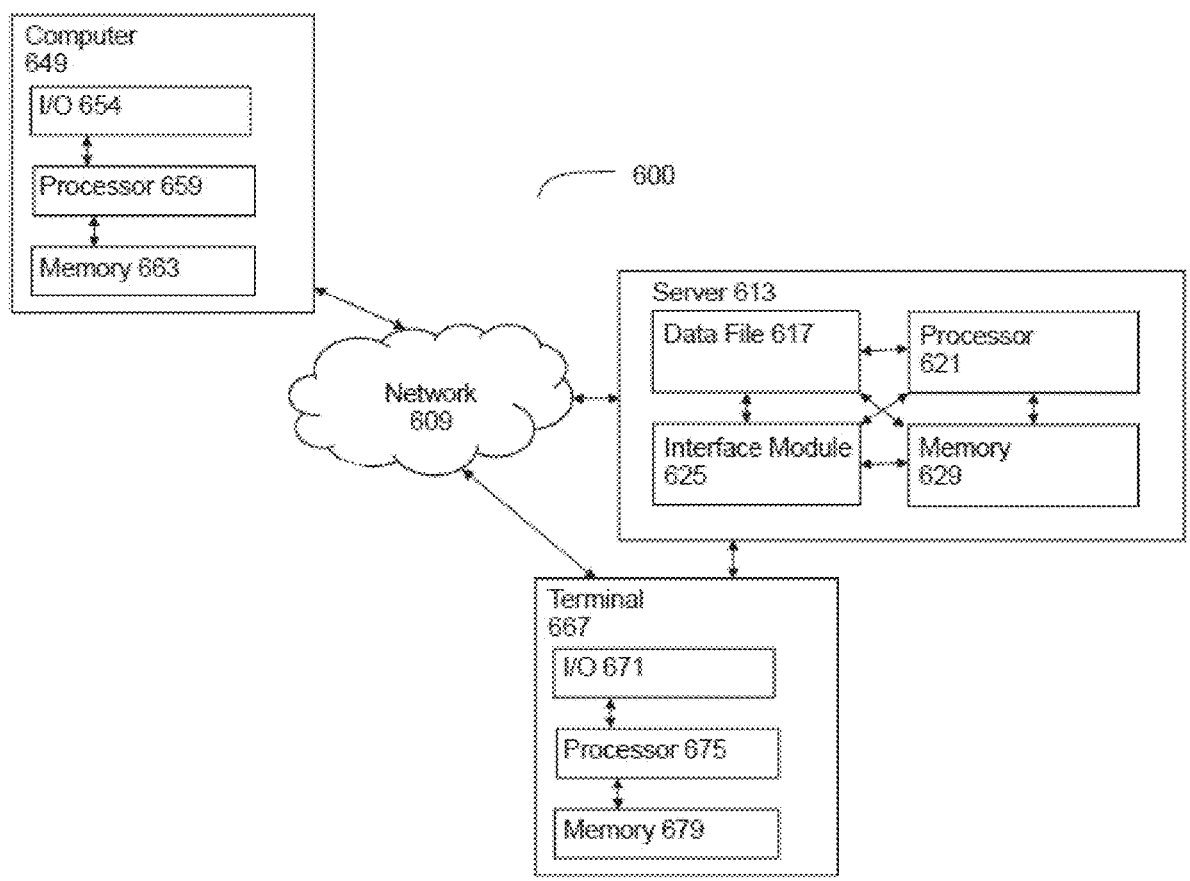
FIG. 7 shows a system of the invention in accordance with certain embodiments.

In an example embodiment shown in FIG. 7, system 600 can include a computer 649 (e.g., laptop, desktop, or tablet). The computer 649 may be configured to communicate across a network 609. Computer 649 includes one or more processor 659 and memory 663 as well as an input/output mechanism 654. Where methods of the invention employ a client/server architecture, operations of methods of the invention may be performed using server 613, which includes one or more of processor 621 and memory 629, capable of obtaining data, instructions, etc., or providing results via interface module 625 or providing results as a file 617. Server 613 may be engaged over network 609 through computer 649 or terminal 667, or server 613 may be directly connected to terminal 667, including one or more processor 675 and memory 679, as well as input/output mechanism 671.

System 600 or machines according to example embodiments of the invention may further include, for any of I/O 649, 637, or 671 a video display unit (e.g., a liquid crystal display (LCD) or a cathode ray tube (CRT)). Computer systems or machines according to some embodiments can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 663, 679, or 629 according to example embodiments of the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

What is claimed is:

1. A cell culture system comprising:
a cell culture chamber comprising a surface to which cells adhere;
one or more pumps in fluidic communication with the cell culture chamber, the one or more pumps operably coupled to one or more perfusion fluid reservoirs and configured to pump culture media into and out of the cell culture chamber via an inlet and an outlet disposed on the cell culture chamber; and
a processor operably connected to the one or more pumps wherein the processor is configured to operate the one or more pumps on a continuous loop of recurring duty cycles such that when one duty cycle ends another duty cycle begins, each recurring duty cycle comprising an on-cycle and an off-cycle that is longer than the on-cycle; and
memory in communication with the processor, wherein the memory contains one or more calculated duty cycle parameters stored as a set of instructions executable by the processor for operating the one or more pumps on the continuous loop of recurring duty cycles, wherein the set of instructions specify for each recurring duty cycle a duration of an on-cycle, a duration of an off-cycle, and an overall duration of the recurring duty cycle, such that each recurring duty cycle has a same average flow rate within the range of laminar flow to thereby avoid pulsatile flow and closely emulate static cell culture.

2. The cell culture system of claim 1, wherein the cell culture system is sized and configured to fit inside an incubator.

3. The cell culture system of claim 1, further comprising a fluid reservoir in fluidic communication with the inlet of the cell culture chamber.

4. The cell culture system of claim 1, wherein, during the on-cycle, the one or more pumps deliver cell culture medium to the cell culture chamber via the inlet and removes waste products from the cell culture chamber via the outlet.

5. The cell culture system of claim 1, wherein during the on-cycle, the one or more pumps force a flow of fluid to and from the cell culture chamber.

6. The cell culture system of claim 5, wherein the fluid comprises a cell culture medium.

7. The cell culture system of claim 1, wherein the duty cycle has a duration of about 60 seconds.

8. The cell culture system of claim 1, wherein the on-cycle lasts for under 20% of the duration of the duty cycle.

9. The cell culture system of claim 1, wherein the average flow rate is less than 1000 µL of fluid per minute.

10. The cell culture system of claim 1, wherein the system calculates the one or more duty cycle parameters based on a desired average flow rate, a heat output of the system, and a desired cell culture temperature inside an incubator.

11. The cell culture system of claim 1, wherein the one or more duty cycle parameters comprise one or more of duration of the duty cycle, percentage of time for the on-cycle, and flow rate during the on-cycle.

* * * * *